(12) United States Patent
Chuang et al.

(10) Patent No.: US 10,092,244 B2
(45) Date of Patent: Oct. 9, 2018

(54) BIOMETRIC DETECTION MODULE WITH DENOISING FUNCTION AND BIOMETRIC DETECTION METHOD THEREOF

(71) Applicant: PIXART IMAGING INC., Hsin-Chu County (TW)

(72) Inventors: Chih-Yuan Chuang, Hsin-Chu County (TW); Cheng-Nan Tsai, Hsin-Chu County (TW); Ming-Tsan Kao, Hsin-Chu County (TW); Ren-Hau Gu, Hsin-Chu County (TW); Yen-Min Chang, Hsin-Chu County (TW)

(73) Assignee: PIXART IMAGING INC., Hsin-Chu County ( * ) Notice: Subject to any disclaimer, the term of this patent is extended or adjusted under 35 U.S.C. 154(b) by 616 days.

(21) Appl. No.: 14/685,782

(22) Filed: Apr. 14, 2015

(65) Prior Publication Data
US 2016/0007929 A1     Jan. 14, 2016

(30) Foreign Application Priority Data
Jul. 8, 2014   (TW) .............................. 103123543 A (51) Int. Cl.
*A61B 5/024*     (2006.01)
*A61B 5/00*      (2006.01)
*A61B 5/1455*    (2006.01)

(52) U.S. Cl.
CPC ........ *A61B 5/7214* (2013.01); *A61B 5/02427* (2013.01); *A61B 5/02438* (2013.01); *A61B 5/14552* (2013.01); *A61B 5/6803* (2013.01); *A61B 5/6815* (2013.01); *A61B 5/725* (2013.01); *A61B 5/02433* (2013.01); *A61B 5/742* (2013.01); *A61B 2562/0238* (2013.01)

(58) Field of Classification Search
CPC .......... A61B 5/1455–5/14558; A61B 5/04216; A61B 5/04244; A61B 5/02427; A61B 5/02433
See application file for complete search history.

(56) References Cited

U.S. PATENT DOCUMENTS 5,971,930 A * 10/1999 Elghazzawi ....... A61B 5/14551
                                                    600/310
7,072,701 B2    7/2006 Chen et al.
(Continued)

FOREIGN PATENT DOCUMENTS

WO   WO 2013/056379   * 10/2011 ........... A61B 5/1455

*Primary Examiner* — Catherine B Kuhlman
(74) *Attorney, Agent, or Firm* — Hauptman Ham, LLP (57) ABSTRACT

A biometric detection module including a light source module, a detection region and a control module is provided. The light source module is configured to emit green light, red light and IR light in a time division manner to illuminate a skin surface. The detection region is configured to detect penetration light emitted from the light source module for illuminating the skin surface and passing through body tissues to correspondingly generate a green light signal, a red light signal and an IR light signal. The control module is configured to determine a filtering parameter according to the green light signal to accordingly filter the red light signal and the IR light signal, and calculate a biometric characteristic according to at least one of the green light signal, a filtered red light signal and a filtered IR light signal.

18 Claims, 8 Drawing Sheets

(56) References Cited

U.S. PATENT DOCUMENTS

| | | | |
|---|---|---|---|
| 2003/0225337 A1* | 12/2003 | Scharf | A61B 5/14551 600/508 |
| 2008/0146892 A1* | 6/2008 | LeBoeuf | A61B 5/486 600/300 |
| 2008/0167564 A1* | 7/2008 | Hete | A61B 5/02405 600/508 |
| 2014/0107493 A1 | 4/2014 | Yuen et al. | |
| 2015/0190063 A1* | 7/2015 | Zakharov | A61B 5/14551 600/301 |
| 2015/0248025 A1* | 9/2015 | Carrara | G02C 3/003 351/158 |

* cited by examiner

BIOMETRIC DETECTION MODULE WITH DENOISING FUNCTION AND BIOMETRIC DETECTION METHOD THEREOF

RELATED APPLICATIONS

The present application is based on and claims priority to Taiwanese Application Number 103123543, filed Jul. 8, 2014, the disclosure of which is hereby incorporated by reference herein in its entirety.

BACKGROUND

1. Field of the Disclosure

This disclosure generally relates to a biometric detection module and, more particularly, to a biometric detection module with denoising function.

2. Description of the Related Art

Conventional pulse oximeters utilize a noninvasive method to monitor the blood oxygenation and the heart rate of a user. A pulse oximeter generally emits a red light beam (wavelength of about 660 nm) and an infrared light be am (wavelength of about 910 nm) to penetrate a part of the human body and detects an intensity variation of the penetrating light based on the feature that the oxyhemoglobin and the deoxyhemoglobin have different absorptivities in particular spectrum, e.g. referring to U.S. Pat. No. 7,072,701 entitled "Method for spectrophotometric blood oxygenation monitoring". After the intensity variations, e.g. photoplethysmographic signals or PPG signals, of the penetrating light of the two wavelengths are detected, the blood oxygenation can then be calculated according to an equation: Blood oxygenation=$100\% \times [HbO_2]/([HbO_2]+[Hb])$, wherein $[HbO_2]$ is an oxyhemoglobin concentration; and $[Hb]$ is a deoxyhemoglobin concentration.

Generally, the intensity variations of the penetrating light of the two wavelengths detected by a pulse oximeter will increase and decrease with heartbeats. This is because blood vessels expand and contract with the heartbeats such that the blood volume that the light beams pass through will change to accordingly change the ratio of light energy being absorbed. Therefore, the absorptivity of blood of different light spectra can be calculated according to the intensity information changing continuously so as to calculate the physiology information, e.g. the oxyhemoglobin and deoxyhemoglobin concentrations, respectively. Finally, the blood oxygenation can be calculated according to the above equation.

However, as the pulse oximeter detects the intensity variation of the penetrating light passing through body tissues, different intensity signals will be detected by detecting different parts of the human body. In addition, when the part of the human body being detected has a relative movement with respect to the pulse oximeter, a disturbed signal can be detected such that it is not possible to calculate correct physiology information. Therefore, a clear PPG signal is difficult to be detected under a condition of a non-static state.

SUMMARY

Accordingly, the present disclosure provides a biometric detection device adaptable to non-static detecting states.

The present disclosure provides a biometric detection module configured to be attached to an eyeglass temple and detect at least one biometric characteristic from a skin region behind ear. The biometric detection module includes a detection unit. The detection unit includes a light source module, a detection region and a control module. The light source module is configured to emit green light, red light and infrared light in a time division manner to illuminate the skin region. The detection region is configured to detect penetrating light emitted from the light source module for illuminating the skin region and passing through body tissues to correspondingly generate a green light signal, a red light signal and an infrared light signal. The control module is configured to control the light source module to emit light, determine a filtering parameter according to the green light signal to accordingly filter the red light signal and the infrared light signal, and calculate the biometric characteristic according to at least one of the green light signal, a filtered red light signal and a filtered infrared light signal.

The present disclosure further provides a biometric detection module configured to detect at least one biometric characteristic from a skin region in concha. The biometric detection module includes a detection unit. The detection unit includes a light source module, a detection region and a control module. The light source module is configured to emit green light, red light and infrared light in a time division manner to illuminate the skin region. The detection region is configured to detect penetrating light emitted from the light source module for illuminating the skin region and passing through body tissues to correspondingly generate a green light signal, a red light signal and an infrared light signal. The control module is configured to control the light source module to emit light, determine a filtering parameter according to the green light signal to accordingly filter the red light signal and the infrared light signal, and calculate the biometric characteristic according to at least one of the green light signal, a filtered red light signal and a filtered infrared light signal.

The present disclosure further provides a biometric detection method of a biometric detection module. The biometric detection module includes a light source module and a detection region, and is configured to detect at least one biometric characteristic from a skin surface. The biometric detection method includes the steps of: emitting, using the light source module, green light, red light and infrared light in a time division manner to illuminate the skin surface; detecting, using the detection region, penetrating light emitted from the light source module for illuminating the skin surface and passing through body tissues to correspondingly generate a green light signal, a red light signal and an infrared light signal; determining a filtering parameter according to the green light signal; filtering the red light signal and the infrared light signal with the filtering parameter to generate a filtered red light signal and a filtered infrared light signal; and calculating the biometric characteristic according to at least one of the green light signal, the filtered red light signal and the filtered infrared light signal.

BRIEF DESCRIPTION OF THE DRAWINGS

Other objects, advantages, and novel features of the present disclosure will become more apparent from the following detailed description when taken in conjunction with the accompanying drawings.

DETAILED DESCRIPTION OF THE EMBODIMENT

It should be noted that, wherever possible, the same reference numbers will be used throughout the drawings to refer to the same or like parts.

The present disclosure provides a biometric detection device adaptable to head accessories and may be attached to glasses or earphone devices, but not limited thereto. The biometric detection device has the function of removing noises caused by the movement. The biometric detection device of the present disclosure may also be attached to other headgears using a securing member, e.g. attaching and detaching from a hat or a cap through a clamp such that it may be mounted while being used so as to improve the practicality thereof.

Figure 1A:
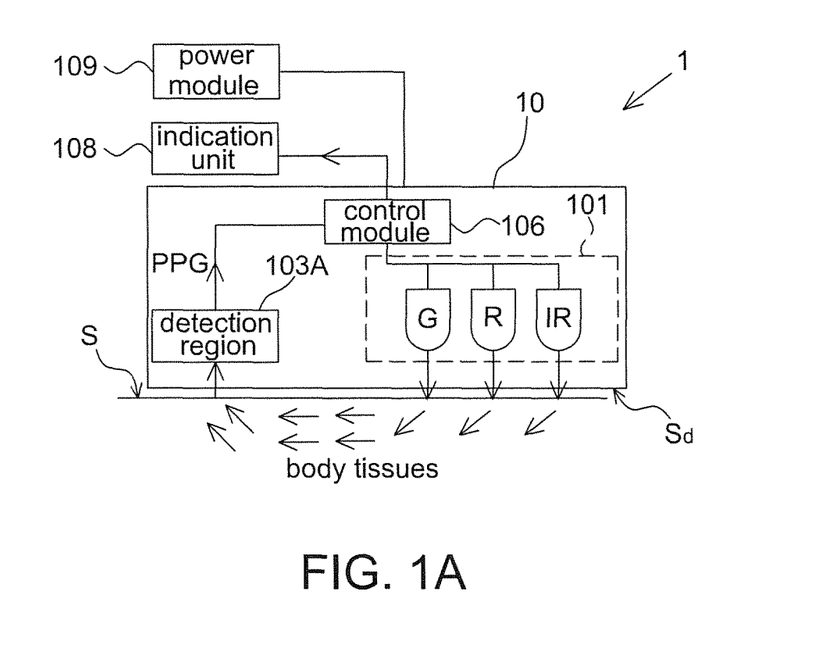
FIG. 1A is a block diagram of a biometric detection module according to one embodiment of the present disclosure.

Referring to FIG. 1A, it is a block diagram of a biometric detection module according to one embodiment of the present disclosure. The biometric detection module includes a light source module 101, a detection region 103A, a control module 106, an indication unit 108 and a power module 109. The light source module 101, the detection region 103A and the control module 106 may form a detection unit 10 for detecting at least one biometric characteristic, e.g., a heart rate, a blood oxygenation and/or a second derivative of photoplethysmogram, from a skin surface S via a detection surface Sd thereof, wherein the principle of detecting the heart rate, the blood oxygenation and the second derivative of photoplethysmogram according to PPG signals is known to the art and thus details thereof are not described herein. The indication unit 108 is configured to show the biometric characteristic through audio or images, e.g. including a speaker module or a display device. The power module 109 is configured to provide power required by the detection unit 10 in operation. It should be mentioned that when the biometric detection module 1 is attached to a head-mounted device (illustrated with examples below), the indication unit 108 and the power module 109 may be shared with the head-mounted device but not included in the biometric detection module 1 as long as they are electrically connected to the biometric detection module 1 for signal transmission.

The light source module 101 includes, for example, at least one light emitting diode, at least one laser diode, at least one organic light emitting diode or other active light sources configured to emit green light, red light and infrared light in a time division manner to illuminate the skin surface S. In one embodiment, the light source module 101 includes a single light source whose emission spectrum is changeable by adjusting a driving parameter (such as the driving current or the driving voltage) so as to emit green light, red light and infrared light, wherein a wavelength of the green light is between, for example, 490 nm and 570 nm, and the red light and the infrared light are those generally used in the biometric detection. In another embodiment, the light source module 101 includes a green light source, a red light source and an infrared light source configured to emit green light, red light and infrared light, respectively.

The detection region 103A is, for example, a semiconductor detection region which includes a plurality of detection pixels each including at least one photodiode configured to convert optical energy to electric signals. The detection region 103A is configured to detect penetrating light emitted from the light source module 101 for illuminating the skin surface S and passing through body tissues so as to correspondingly generate a green light signal, a red light signal and an infrared light signal, wherein the green light signal, the red light signal and the infrared light signal are referred to photoplethysmographic signals or PPG signals.

Figure 1B:
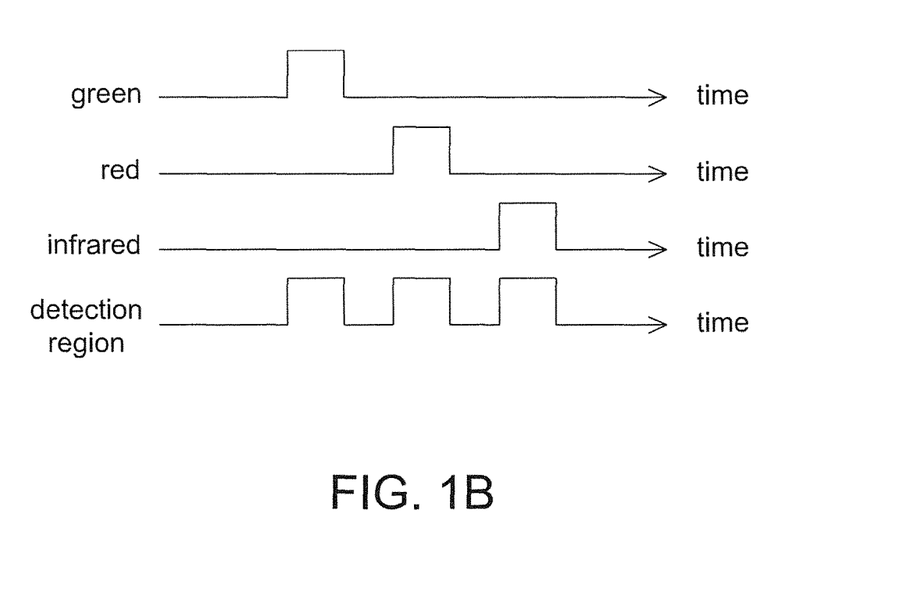
FIG. 1B is an operational schematic diagram of a biometric detection module according to one embodiment of the present disclosure.

The control module 106 is configured to control the light source module 101 to emit light in a time division manner and corresponding to the light detection of the detection region 103A, as shown in FIG. 1B, wherein the signal sequence shown in FIG. 1B is only intended to illustrate but not to limit the present disclosure. When the biometric detection module 1 is adapted to a head accessory, a relative position between the biometric detection module 1 and the skin surface S may not be stable such that noises are generated in the detected signals (i.e. the PPG signals). Accordingly, in the present disclosure the green light signal is used to determine a filtering parameter configured to filter the red light signal and the infrared light signal.

Figure 2A:
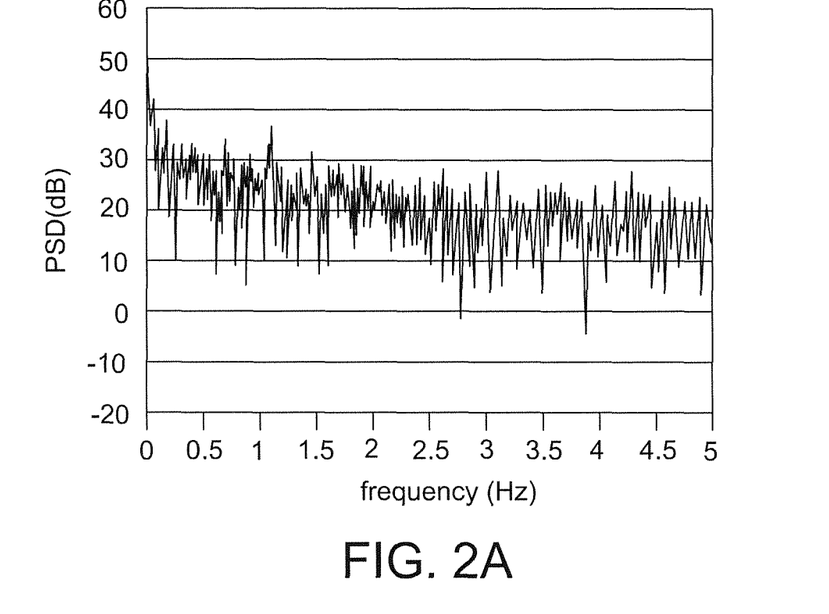
FIGS. 2A and 2B are detected signals of a biometric detection module in frequency domain according to some embodiments of the present disclosure.
Figure 2B:
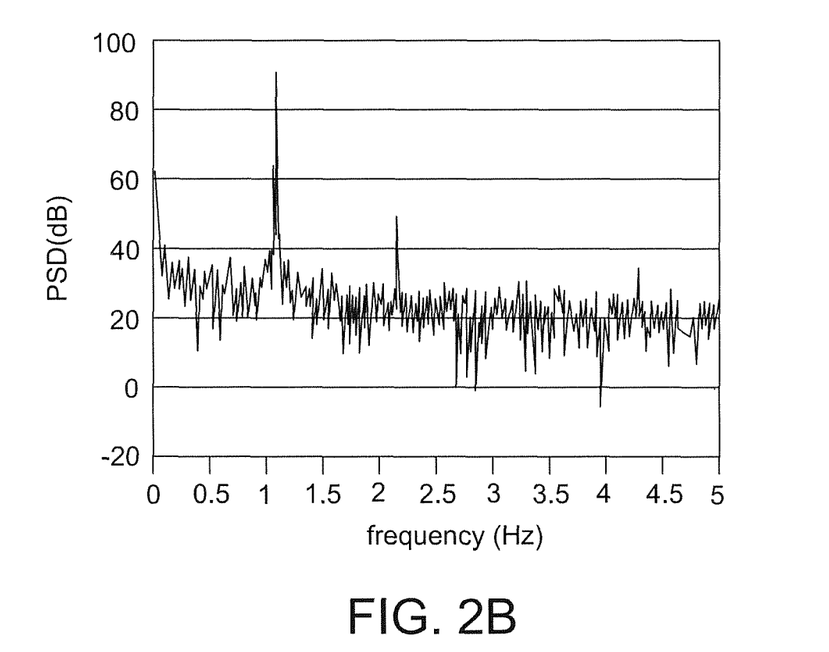

For example, referring to FIG. 2A, it is a schematic diagram of the power spectral density (PSD) in frequency domain converted from the red light signal or the infrared light signal detected by the biometric detection module 1, wherein a main frequency in the frequency domain signals being detected is not obvious due to the noises. Referring to FIG. 2B, it is a schematic diagram of the power spectral density (PSD) in frequency domain converted from the green light signal detected by the biometric detection module 1. As $SPO_2$ has a higher absorption of the green light, the filtering parameter is determined according to a frequency domain green light signal (as FIG. 2B), e.g. the signal component at 1 Hz being served as a basic frequency herein, wherein the control module 106 converts the PPG signals to the frequency domain using, for example, Fourier transform, wavelet analysis or other algorithms. The control module 106 then filters the red light signal and the infrared light signal with the filtering parameter so as to respectively generate a filtered red light signal and a filtered infrared light signal. In one embodiment, the filtered red light signal is obtained by converting signal components at the basic frequency of a frequency domain red light signal (e.g. FIG. 2A) back to time domain, and the filtered infrared light signal is obtained by converting signal components at the basic frequency of a frequency domain infrared light signal (e.g. FIG. 2A) back to the time domain.

The control module 106 may calculate the biometric characteristic according to at least one of the green light signal, the filtered red light signal and the filtered infrared light signal. In one embodiment, the heart rate and the second derivative of photoplethysmogram are obtained according to one of the green light signal, the filtered red light signal and the filtered infrared light signal; and the blood oxygenation is obtained according to the filtered red light signal and the filtered infrared light signal.

It should be mentioned that when the biometric detection module 1 is attached to other devices, e.g. an earphone, a part of functions of the control module 106 may be performed by a processor of said devices. For example in some embodiments, the biometric detection module 1 detects PPG signals, but the processing and filtering of the PPG signals and the calculation of the biometric characteristic may be performed by an external processor.

Figure 3A:
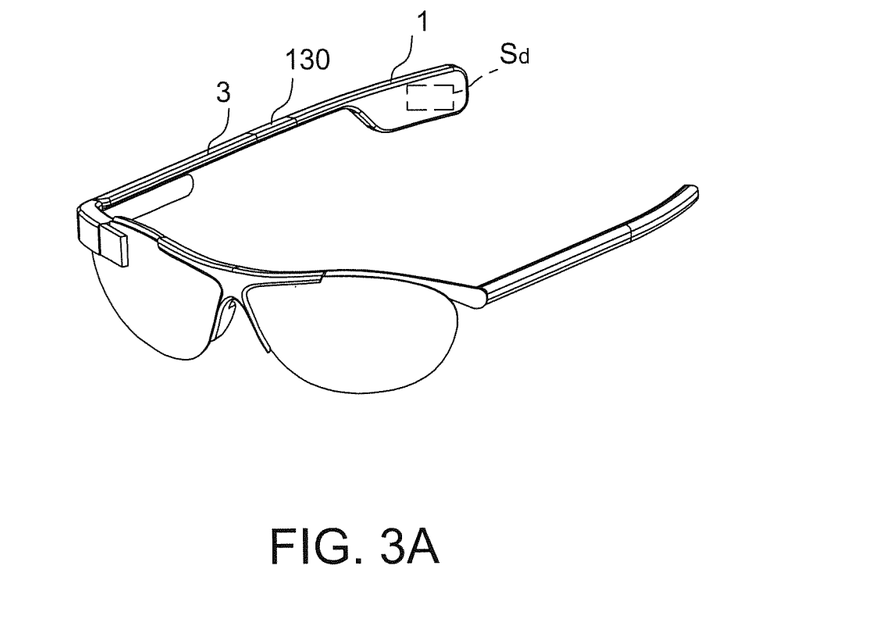
FIGS. 3A and 3B are schematic diagrams of a biometric detection module applied to glasses according to some embodiments of the present disclosure.
Figure 3B:
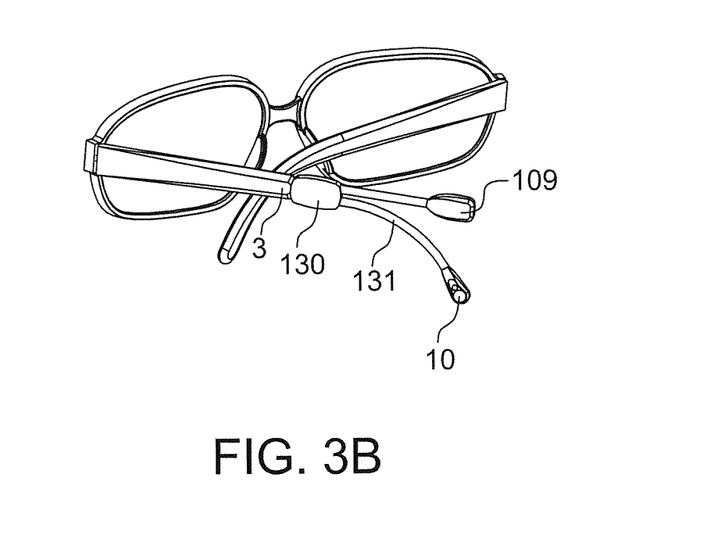
Figure 4:
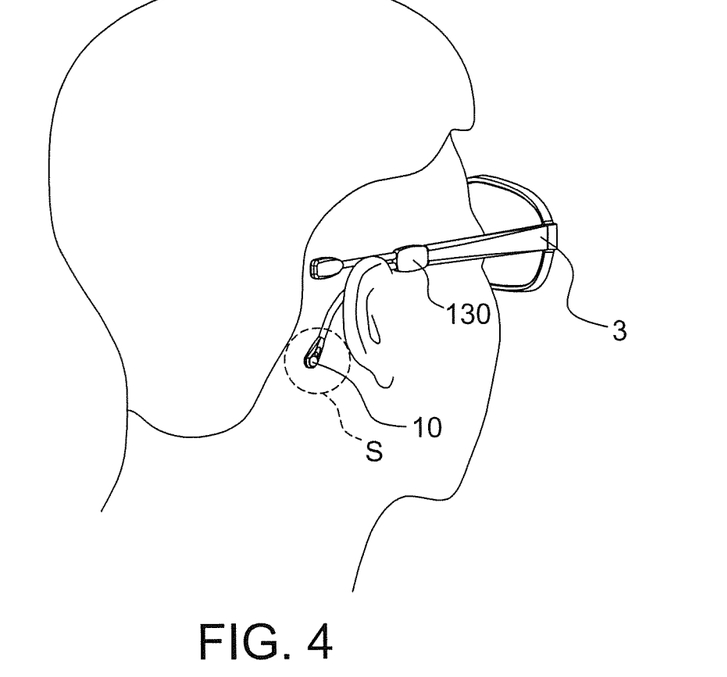
FIG. 4 is a schematic diagram of wearing the glasses to which a biometric detection module of some embodiments of the present disclosure is applied.

Referring to FIGS. 3A, 3B and 4, FIGS. 3A and 3B are schematic diagrams of a biometric detection module 1 applied to glasses and FIG. 4 is a schematic diagram of wearing the glasses to which the biometric detection module 1 is applied. Herein, the biometric detection module 1 is attached to an eyeglass temple 3 and configured to detect at least one biometric characteristic from a skin region behind ear S (as FIG. 4) corresponding to the temporal bone. In some embodiments, the biometric detection module 1 includes a joint portion 130 and a detection unit 10, wherein as mentioned above the detection unit 10 includes a light source module 101, a detection region 103A and a control module 106, and has a detection surface Sd configured to be attached to the skin region behind ear S. That is, said skin surface S herein is referred to a skin region behind ear. The joint portion 130 is configured to combine with the eyeglass temple 3. In some embodiments, the biometric detection module 1 is fixed on the eyeglass temple 3 through the joint portion 130. In other embodiments, the biometric detection module 1 is attachable and detachable from the eyeglass temple 3 through the joint portion 130.

In addition, for facilitating the position adjustment of the biometric detection module 1 to allow the detection surface Sd thereof to be accurately attached to the skin region behind ear S, the biometric detection module 1 further includes an adjustment portion 131 (as FIG. 3B) connected between the joint portion 130 and the detection unit 10 for adjusting a position of the detection unit 10, wherein the adjustment portion 131 is made of soft material which deforms under an external force and keeps its shape without the external force. In addition, the biometric detection module 1 may be formed as a signal branch as shown in FIG. 3A or formed with a plurality of branches as shown in FIG. 3B, wherein different branches are used to dispose different components. For example, in FIG. 3A a power module and a detection unit are disposed at the same branch, but in FIG. 3B the power module 109 and the detection unit 10 are disposed at different branches.

In addition, when the biometric detection module 1 is attached to glasses with the display function, e.g. including an LCOS display, the glasses may show the biometric characteristic detected by the biometric detection module 1 so as to form an eyeglass module capable of detecting biometric characteristics.

Figure 5:
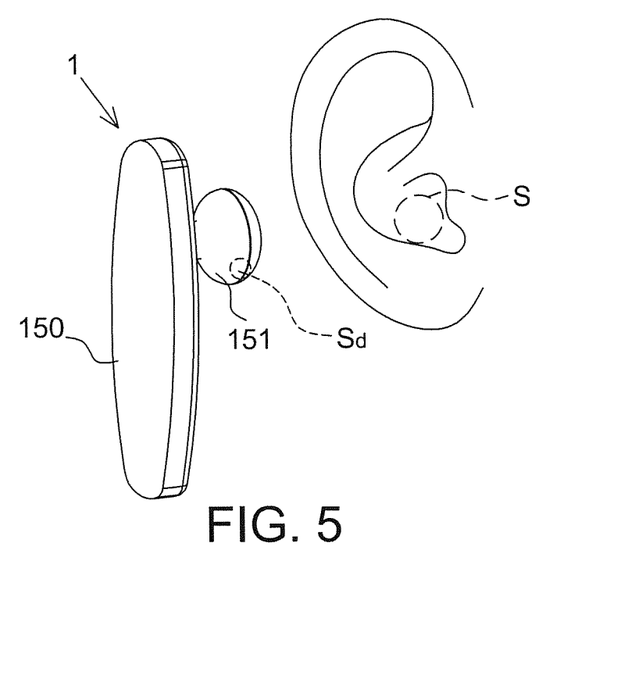
FIG. 5 is a schematic diagram of a biometric detection module applied to an earphone according to one embodiment of the present disclosure.

Referring to FIG. 5, in another embodiment the biometric detection module 1 is configured to detect at least one biometric characteristic from a skin region in concha S. Herein, the biometric detection module 1 includes a main body 150 and a protrusion portion 151 protruding outward from the main body 150 to be put in the concha. The detection unit is disposed at the protrusion portion 151 and has a detection surface Sd configured to be attached to the skin region in concha S. That is, herein said skin surface S is a skin region in concha. In addition, the indication unit 108 and the power module 109 are disposed at the main body 150. For example, the indication unit 108 is a display device or a speaker module for showing the biometric characteristic detected by the biometric detection module 1 through images or audio. In addition, in this embodiment the detection unit also includes a light source module 101, a detection region 103A and a control module 106 whose functions are described above and thus details thereof are not repeated herein.

In one embodiment, the biometric detection module 1 is attached to an earphone device, e.g. a Bluetooth earphone. It should be mentioned that although in FIG. 5 the biometric detection module 1 is shown to have an earphone shape, when the biometric detection module 1 is arranged as individual element without being attached to the earphone, it may have other shapes without being limited to that shown in FIG. 5. In addition, for facilitating the mounting, the biometric detection module 1 may include other structure(s) configured to be mounted on the outer ear or the head without particular limitations.

Figure 6:
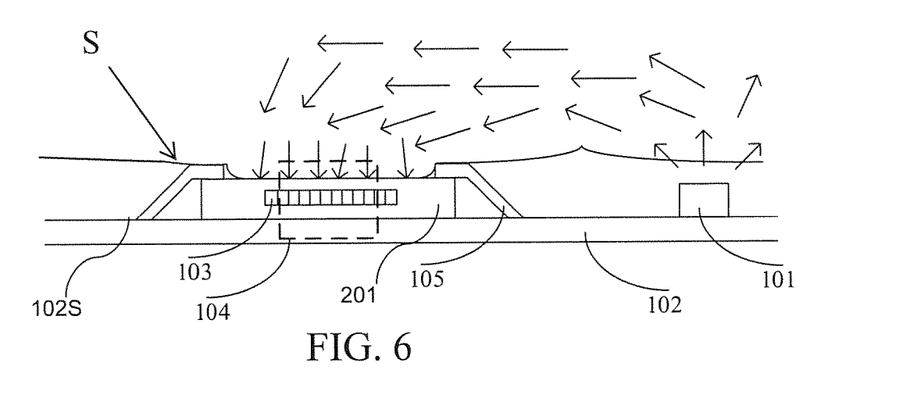
FIG. 6 is a schematic diagram of a thin biometric detection module according to one embodiment of the present disclosure.
Figure 9A:
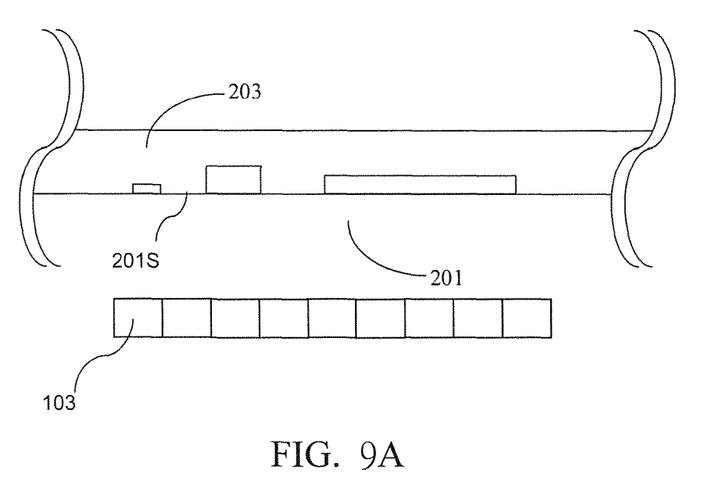
FIGS. 9A and 9B are cross-sectional views of the thin semiconductor structure of a biometric detection module according to some embodiments of the present disclosure.
Figure 9B:
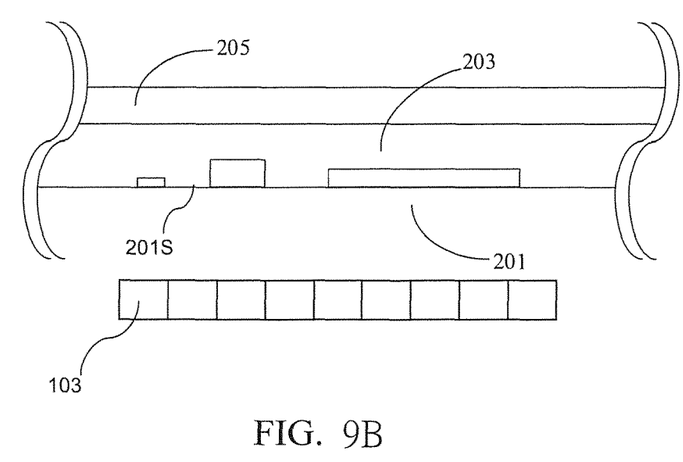

FIG. 6 shows a detection unit of a thin biometric detection module according to one embodiment of the present disclosure, which includes at least one light source module 101, a substrate 102, a plurality of detection pixels 103 and a plurality of contact points 105, wherein the detection pixels 103 form an optical semiconductor detection region 103A, which has a thin semiconductor structure 104 (further illustrated in FIGS. 9A and 9B). The contact points 105 are configured to electrically connect the optical semiconductor detection region 103A to the substrate 102 for being controlled by a control module 106 (as shown in FIG. 1A), wherein the detection pixels 103 may be arranged in a chip 201 and the contact points 105 are served as outward electrical contacts of the chip 201. The light source module 101 is also electrically connected to the substrate 102, and the control module 106 is configured to control the light source module 101 to illuminate the skin surface S such that the emitted light may enter body tissues (e.g. the above skin region behind ear or in concha) of a user. Meanwhile, the control module 106 is also configured to control the detection pixels 103 to detect light transmitting out from the body tissues. As vessels and blood in the body tissues have different optical properties, by arranging specific light source module 101 the biometric characteristic may be identified according to the optical images detected by the detection pixels 103.

More specifically, the control module 106 may be integrated in the chip 201 or disposed on the substrate 102 (on the same or different surfaces of the substrate 102 with respect to the chip 201) and configured to control the light source module 101 and the optical semiconductor detection region 103A. The substrate 102 has a substrate surface 102S on which the chip 201 and the light source module 101 are disposed. In this embodiment, in order to effectively reduce the total size, a relative distance between the chip 201 and the light source module 101 is preferably smaller than 8 millimeters.

In some embodiments, the contact points 105 may be the lead frame structure. In other embodiments, the contact points 105 may be bumps, the ball grid array or wire leads, but not limited thereto.

In some embodiments, an area of the detection region 103A is larger than 25 mm². The optical semiconductor detection region may successively capture images at a frame rate higher than hundreds of frames per second. For example, the control module 106 may control the optical semiconductor detection region 103A to capture optical images at a frame rate higher than 300 frames per second and control the light source module 101 to emit light corresponding to the image capturing.

Figure 7:
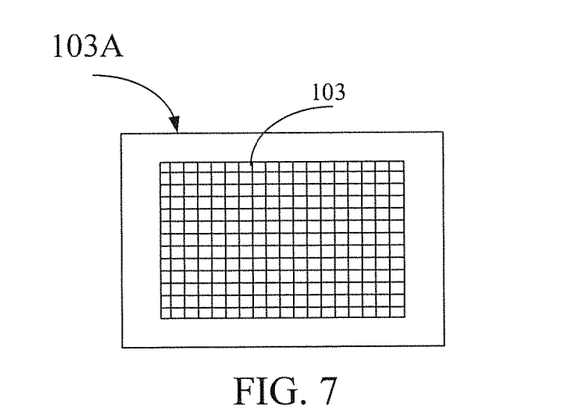
FIG. 7 is an upper view of the detection region of a biometric detection module according to one embodiment of the present disclosure.

FIG. 7 is an upper view of the optical semiconductor detection region 103A according to one embodiment of the present disclosure. In detecting biometric characteristics, e.g. the blood oxygenation, the heart rate (pulse) and the blood pressure, as the skin surface S does not have fast relative movement with respect to the detection surface Sd, the size of the detection region 103A does not obviously affect the detected result. FIG. 7 shows the detection region 103A as a rectangular type, and a ratio of the transverse and longitudinal widths may be between 0.5 and 2. Accordingly, no matter which of the biometric characteristics such as the vein texture, blood oxygenation, pulse, blood pressure or second derivative of photoplethysmogram of a user is to be detected, a user only needs to attach the detection region 103A to the skin surface S. An area of the detection region 103A is at least larger than 25 mm².

Figure 8A:
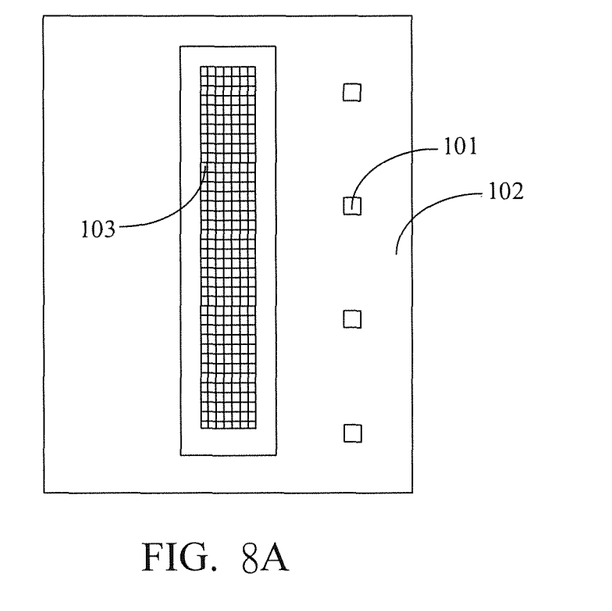
FIGS. 8A and 8B are upper views of a biometric detection module according to some embodiments of the present disclosure.
Figure 8B:
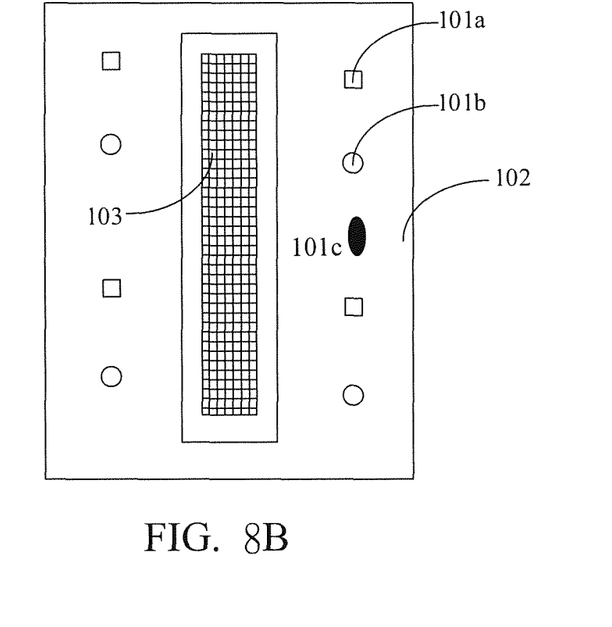

FIGS. 8A and 8B are upper views of a thin biometric detection module according to some embodiments of the present disclosure, which show the arrangement of the light source and the application using a plurality of light sources. In FIG. 8A, the light source module 101 is shown to be arranged at one side of a plurality of detection pixels 103 and electrically connected to the substrate 102. It should be noted that in this embodiment, although the light source module 101 is arranged at one side of the detection pixels 103, as the light may penetrate into the body tissues of the user, the position of the light source module does not affect the direction of the detection unit as long as the skin surface is continuously illuminated by the light source module during the detection process.

In FIG. 8B, three different light sources 101a, 101b and 101c are shown. In this embodiment, the term "different light sources" is referred to the light sources emitting light of different wavelengths. As different components in the body tissues have different optical responses toward different light wavelengths, e.g. having different absorptions, by detecting different light sources the biometric characteristic associated with the light wavelengths may be derived and the correction may be performed according to the detected images associated with different light sources so as to obtain correct detected results. For example, the oxygen component in the blood has different absorptions associated with different light colors, and thus by detecting the energy of different light colors the blood oxygenation may be derived. In other words, the thin biometric detection module according to the embodiment of the present disclosure may include three light sources 101a, 101b and 101c respectively emitting light of different wavelengths, e.g. red light, infrared light and green light. And the optical semiconductor detection region 103A may include three types of detection pixels configured to respectively detect different light wavelengths emitted from the light sources.

For example, if the blood oxygenation is to be detected, two light wavelengths close to the absorption wavelength 805 nm of $HbO_2$ and Hb may be selected, e.g. about 660 nm and 940 nm. Or the light wavelength between 730 nm and 810 nm or between 735 nm and 895 nm may be selected. The blood oxygenation may be derived according to the difference of light absorption of blood between the two light wavelengths. The wavelength of the green light is selected to be within the green light spectrum without particular limitations. The related detection technology is well known to the art and thus details thereof are not described herein.

According to FIGS. 8A and 8B, it is known that a plurality of light sources may be adopted in the present disclosure and is not limited to use only a single light source or two light sources. Furthermore, according to the biometric characteristic to be detected, different detection pixels may be arranged corresponding to more light sources, and the position of the light sources does not have particular limitations. In the thin structure, the biometric detection module of the present disclosure may be applied to detect various biometric characteristics. Different light sources may also be adopted in order to detect biometric characteristics. If it is desired to acquire uniform images, identical light sources may be arranged at both sides of same detection regions such that light may enter the body tissues from two sides of the same detection regions.

FIGS. 9A and 9B are cross-sectional views of the optical semiconductor detection region according to some embodiments of the present disclosure, which are partial schematic diagrams of the thin semiconductor structure 104. FIG. 9A is an embodiment in which a planar layer 203 also has the abrasion-proof ability. For example, the planar layer 203 made of polyimide material may have enough abrasion-proof ability to be adapted to the present disclosure. That is, the planar layer 203 is also served as the abrasion-proof layer herein. The planar layer 203 is formed on the top of the chip structure 201 and on the chip surface 201S to overlay the optical semiconductor detection region for protecting the semiconductor structure 104. As the top of the chip structure 201 may have many convexes and concaves (as shown in the figure) after the metal layer and the electrode are formed thereon due to the semiconductor layout, the non-uniform has a negative effect to the optical detection and a weaker weather-proof ability. Accordingly, the planar layer 203 is formed on the top to allow the thin semiconductor structure 104 to have a flat surface to be suitable to the present disclosure. In the present disclosure, as the thin semiconductor structure 104 is exposed to air and directly in contact with the user's body frequently, a better abrasion-proof ability is required. In the semiconductor manufacturing technology nowadays, the polyimide-based material may be selected as the abrasion-proof material. Meanwhile, the planar layer 203 is preferably transparent to visible or invisible light according to the selection of the light source. In addition, the abrasion-proof material may be glass material or the like. For example, the abrasion-proof layer is a glass layer.

It should be noted that in order to reduce the diffusion of light when passing through the planar layer 203 to blur the image, preferably a distance from the surface of the semiconductor structure 104 to the surface of the chip structure 201, i.e. the thickness of the planar layer 203 herein, is limited to be smaller than 100 micrometers. That is, a distance from the chip surface 201S to an upper surface of the planar layer 203 (i.e. the abrasion-proof layer) is preferably smaller than 100 micrometers. When detecting the biometric characteristic, the upper surface of the planar layer 203 is configured as the detection surface Sd to be directly in contact with a skin surface S such that light emitted from the light source module 101 directly illuminates the skin surface S and sequentially passes through the body tissues and the planar layer 203 to be detected by the optical semiconductor detection region. In one embodiment, a distance between an emission surface of the light source module 101 and the substrate surface 102S is identical to a distance between the upper surface of the planar surface 203 and the substrate surface 102S. That is, when an emission surface of the light source module 101 and an upper surface of the planar surface 203 have an identical height, the light emitted by the light source module 101 may efficiently pass through the skin surface to enter the part of human body and be detected by the optical semiconductor detection region.

The difference between FIG. 9B and FIG. 9A is that the planar layer 203 in FIG. 9B does not have enough abrasion-proof ability, and thus another abrasion-proof layer 205 is formed upon the planar layer 203. Similarly, in order to reduce the diffusion of light when passing through the planar layer 203 and the abrasion-proof layer 205, in this embodiment a total thickness of the planar layer 203 and the abrasion-proof layer 205 is preferably limited to be smaller than 100 micrometers. In this embodiment, the planar layer 203 may be any material without considering the abrasion-proof ability thereof and the abrasion-proof layer 205 may be made of polyimide-based abrasion-proof material. In addition, the abrasion-proof material may be glass material or the like. For example, the abrasion-proof layer is a glass layer.

In some embodiments, it is possible to arrange a plurality of detection regions, e.g. arranging a plurality of linear detection regions along a predetermined direction or inserting light sources between a plurality of linear detection regions. For example, the linear optical semiconductor detection regions may be arranged adjacent to each other, or the linear optical semiconductor detection regions and a plurality of light sources may be arranged alternatively so as to obtain a better optical imaging. As the detection principle is not changed, details thereof are not described herein.

Said substrate 102 is configured to electrically connect the light source module 101 and the detection pixels 103 and to allow the light source module to emit light to enter the body tissues, and thus the substrate may be a flexible soft substrate or a hard substrate made of hard material without particular limitations.

In the embodiment of a thin type structure, the optical semiconductor detection region may be directly attached to the skin surface of a user without other optical mechanism(s) to perform the image scaling and the light propagation. And thin and durable features thereof are suitable to be applied to head accessories or ear accessories, e.g., the glasses and earphones.

In some embodiments, according to the adopted light source, different light filters may be formed during manufacturing the detection pixels to allow the desired light to pass through the filter and be received by the detection pixels. The filters may be formed in conjunction with the semiconductor manufacturing process on the detection pixels using the conventional technology or formed on the detection pixels after the detection pixels are manufactured. In addition, by mixing the filtering material in the protection layer and/or the planar layer, the protection layer and/or the planar layer may have the optical filtering function. That is, in the embodiment of the present disclosure, said different detection pixels may be referred to the detection pixels with different light filters but not referred to the detection pixels with different structures.

It is appreciated that in order to reduce the size, the biometric detection module 1 is illustrated by the embodiment shown in FIG. 6, but not limited thereto. In some embodiments, other optical mechanism(s) may be disposed between the light source module 101 and the skin surface S to be detected or between the detection region 103A and the skin surface S to be detected according to different applications.

Figure 10:
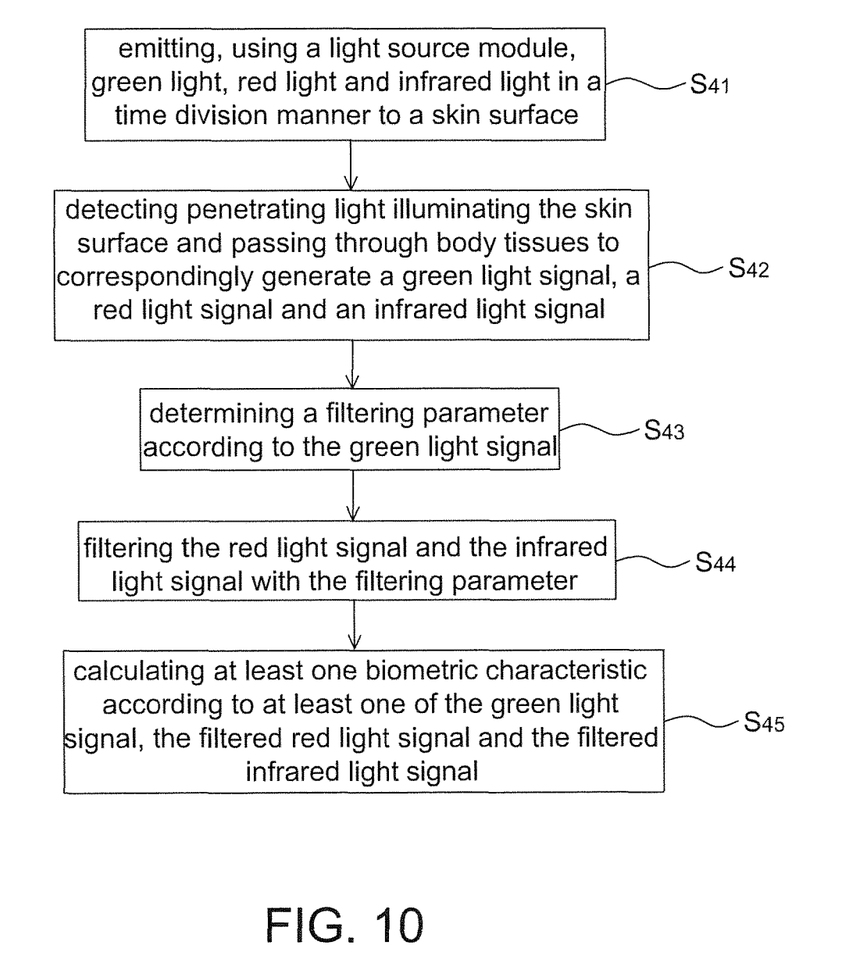
FIG. 10 is a flow chart of a biometric detection method of a biometric detection module according to one embodiment of the present disclosure.

Referring to FIG. 10, it is a flow chart of a biometric detection method of a biometric detection module according to one embodiment of the present disclosure, which includes the steps of: emitting, using a light source module, green light, red light and infrared light in a time division manner to a skin surface (Step $S_{41}$); detecting, using a semiconductor detection region, penetrating light illuminating the skin surface and passing through body tissues to correspondingly generate a green light signal, a red light signal and an infrared light signal (Step $S_{42}$); determining a filtering parameter according to the green light signal (Step $S_{43}$); filtering the red light signal and the infrared light signal with the filtering parameter to generate a filtered red light signal and a filtered infrared light signal (Step $S_{44}$); and calculating at least one biometric characteristic according to at least one of the green light signal, the filtered red light signal and the filtered infrared light signal (Step $S_{45}$).

Referring to FIGS. 1A-2B, 6 and 10 together, details of the present embodiment are illustrated hereinafter.

Steps $S_{41}$-$S_{42}$: The light control module 106 controls the light source module 101 to emit green light, red light and infrared light in a time division manner to illuminate a skin surface S, and controls the detection region 103A to detect penetrating light emitted from the light source module 101 for illuminating the skin surface S and passing through body tissues corresponding to the light emission of the light source module 101 (as FIG. 1B) so as to correspondingly generate a green light signal, a red light signal and an infrared light signal, wherein the green light signal, the red light signal and the infrared light signal are PPG signals. The skin surface S is determined according to the application of the biometric detection module 1.

Step $S_{43}$: The control unit 103 converts, using the built-in algorithm, the green light signal to frequency domain so as to generate a frequency domain green light signal (e.g. FIG. 2B), and determines a basic frequency of the frequency domain green light signal to be served as a filtering parameter, e.g. frequency components at 1 Hz shown in FIG. 2B.

Step $S_{44}$: The control module 106 also converts the red light signal and the infrared light signal to the frequency domain to generate a frequency domain red light signal and a frequency domain infrared light signal as shown in FIG. 2A, and as the noise level is too high, the main frequency component is not identifiable. The control module 106 then converts the signal components associated with the basic frequency (e.g. 1 Hz) of the frequency domain red light signal and the frequency domain infrared light signal back to time domain according to the filtering parameter determined in the Step $S_{43}$ so as to generate a filtered red light signal and a filtered infrared light signal, wherein the filtered red light signal and the filtered infrared light signal are filtered PPG signals.

Step $S_{45}$: Finally, as most of movement noises in the filtered red light signal and the filtered infrared light signal are removed, the control module 106 may calculate the biometric characteristic accordingly, wherein the method of calculating the blood oxygenation according to the red light PPG signal and the infrared light PPG signal is known to the art and thus details thereof are not described herein. In addition, the second derivative of photoplethysmogram is obtainable according to a single PPG signal, and as $SPO_2$ has a higher absorption of the green light, the control module 106 may obtain the second derivative of photoplethysmogram and the heart rate according to one of the green light signal, the filtered red light signal and the filtered infrared light signal.

As mentioned above, the conventional biometric detection module may generate larger noises when detecting a moving skin surface, and thus correct biometric characteristics are difficult to be detected. Therefore, the present disclose further provides a biometric detection module (FIGS. 1A and 6) and a biometric detection method thereof (FIG. 10) that determine a filtering parameter according to a green light signal for removing noises in a red light signal and an infrared light signal thereby improving the detection accuracy. In addition, due to its thin structure, the biometric detection module of the present disclosure is adaptable to various head accessories.

Although the disclosure has been explained in relation to its preferred embodiment, it is not used to limit the disclosure. It is to be understood that many other possible modifications and variations can be made by those skilled in the art without departing from the spirit and scope of the disclosure as hereinafter claimed.

What is claimed is:

1. A biometric detection module, configured to be attached to an eyeglass temple and detect at least one biometric characteristic from a skin region behind an ear, the biometric detection module comprising:
   a detection unit comprising:
      a light source module configured to emit green light, red light and infrared light in a time division manner to illuminate the skin region;
      a detection region configured to detect penetrating light emitted from the light source module for illuminating the skin region and passing through body tissues to correspondingly generate a green light signal, a red light signal and an infrared light signal; and
      at least one processor configured to
         control the light source module to emit light,
         convert the green light signal to frequency domain to determine a filtering parameter according to a frequency domain green light signal,
         respectively convert the red light signal and the infrared light signal to a frequency domain red light signal and a frequency domain infrared light signal,
         filter the frequency domain red light signal and the frequency domain infrared light signal using the filtering parameter, to obtain a filtered red light signal and a filtered infrared light signal, respectively, and
         calculate the biometric characteristic according to at least one of the green light signal, the filtered red light signal and the filtered infrared light signal; and
   an abrasion-proof layer covering the detection region and having an upper surface as a detection surface, wherein
      a thickness of the abrasion-proof layer is smaller than 100 micrometers, and
      the upper surface is configured to be in contact with the skin region when detecting the biometric characteristic such that the light emitted from the light source module illuminates the skin region and sequentially passes through the body tissues and the abrasion-proof layer to be detected by the detection region.

2. The biometric detection module as claimed in claim 1, further comprising:
   a joint portion configured to combine with the eyeglass temple; and
   an adjustment portion connected between the joint portion and the detection unit, and configured to adjust a position of the detection unit,
   wherein the detection surface is configured to be attached to the skin region behind the ear.

3. The biometric detection module as claimed in claim 1, wherein the at least one biometric characteristic comprises a heart rate, a blood oxygenation and a second derivative of photoplethysmogram.

4. The biometric detection module as claimed in claim 3, wherein the at least one processor is configured to
   calculate the heart rate and the second derivative of photoplethysmogram according to one of the green light signal, the filtered red light signal and the filtered infrared light signal, and
   calculate the blood oxygenation according to the filtered red light signal and the filtered infrared light signal.

5. The biometric detection module as claimed in claim 1, wherein the filtering parameter is a basic frequency of the frequency domain green light signal.

6. The biometric detection module as claimed in claim 5, wherein the at least one processor is configured to
   obtain the filtered red light signal by converting signal components at the basic frequency of the frequency domain red light signal back to time domain, and
   obtain the filtered infrared light signal by converting signal components at the basic frequency of the frequency domain infrared light signal back to the time domain.

7. The biometric detection module as claimed in claim 1, wherein the biometric detection module is attached to glasses with a display function for showing the biometric characteristic.

8. A biometric detection module, configured to detect at least one biometric characteristic from a skin region in a concha, the biometric detection module comprising:
   a detection unit comprising:
      a light source module configured to emit green light, red light and infrared light in a time division manner to illuminate the skin region;
      a detection region configured to detect penetrating light emitted from the light source module for illuminating the skin region and passing through body tissues to correspondingly generate a green light signal, a red light signal and an infrared light signal; and
      at least one processor configured to
         control the light source module to emit light,
         convert the green light signal to frequency domain to determine a filtering parameter according to a frequency domain green light signal,
         respectively convert the red light signal and the infrared light signal to a frequency domain red light signal and a frequency domain infrared light signal,
         filter the frequency domain red light signal and the frequency domain infrared light signal using the filtering parameter determined from the frequency domain green light signal, to obtain a filtered red light signal and a filtered infrared light signal, and
         calculate the biometric characteristic according to at least one of the green light signal, the filtered red light signal and the filtered infrared light signal; and
   an abrasion-proof layer covering the detection region and having an upper surface as a detection surface, wherein
      a thickness of the abrasion-proof layer is smaller than 100 micrometers, and the upper surface is configured to be in contact with the skin region when detecting the biometric characteristic such that the light emitted from the light source module illuminates the skin region and sequentially passes through the body tissues and the abrasion-proof layer to be detected by the detection region.

9. The biometric detection module as claimed in claim 8, further comprising:
a main body;
a protrusion portion protruding outward from the main body and configured to be put in the concha;
a power module disposed in the main body and configured to provide power to the detection unit, and
an indication unit disposed in the main body and configured to show the biometric characteristic,
wherein the detection unit is at the protrusion portion, and the detection surface is configured to be attached to the skin region in the concha.

10. The biometric detection module as claimed in claim 8, wherein the at least one biometric characteristic comprises a heart rate, a blood oxygenation and a second derivative of photoplethysmogram.

11. The biometric detection module as claimed in claim 10, wherein the at least one processor is configured to
calculate the heart rate and the second derivative of photoplethysmogram according to one of the green light signal, the filtered red light signal and the filtered infrared light signal, and
calculate the blood oxygenation according to the filtered red light signal and the filtered infrared light signal.

12. The biometric detection module as claimed in claim 8, wherein the filtering parameter is a basic frequency of the frequency domain green light signal.

13. The biometric detection module as claimed in claim 12, wherein the at least one processor is configured to
obtain the filtered red light signal by converting signal components at the basic frequency of the frequency domain red light signal back to time domain, and
obtain the filtered infrared light signal by converting signal components at the basic frequency of the frequency domain infrared light signal back to the time domain.

14. The biometric detection module as claimed in claim 8, wherein the detection region comprises photodiodes respectively configured to detect the red light, the infrared light and the green light.

15. The biometric detection module as claimed in claim 8, wherein the biometric detection module is attached to an earphone.

16. A biometric detection method of a biometric detection module, the biometric detection module comprising a light source module, an abrasion-proof layer and a detection region and configured to detect at least one biometric characteristic from a skin surface, wherein the abrasion-proof layer covers the detection region, has an upper surface as a detection surface and has a thickness smaller than 100 micrometers, and the upper surface is in contact with the skin surface when detecting the biometric characteristic, the biometric detection method comprising:
emitting, using the light source module, green light, red light and infrared light in a time division manner to illuminate the skin surface;
detecting, using the detection region, penetrating light emitted from the light source module for illuminating the skin surface and sequentially passing through body tissues and the abrasion-proof layer to correspondingly generate a green light signal, a red light signal and an infrared light signal;
converting the green light signal to frequency domain and determining a filtering parameter according to a frequency domain green light signal;
converting the red light signal and the infrared light signal respectively to a frequency domain red light signal and a frequency domain infrared light signal;
filtering the frequency domain red light signal and the frequency domain infrared light signal with the filtering parameter and generating a filtered red light signal and a filtered infrared light signal; and
calculating the biometric characteristic according to at least one of the green light signal, the filtered red light signal and the filtered infrared light signal.

17. The biometric detection method as claimed in claim 16, wherein the determining comprises:
taking a basic frequency of the frequency domain green light signal as the filtering parameter.

18. The biometric detection method as claimed in claim 17, further comprising:
converting signal components at the basic frequency of the frequency domain red light signal and the frequency domain infrared light signal back to time domain to generate the filtered red light signal and the filtered infrared light signal.

* * * * *